US012629195B2

(12) United States Patent
Batchelor et al.

(10) Patent No.: US 12,629,195 B2
(45) Date of Patent: May 19, 2026

(54) SUPERHYDROPHOBIC OR SUPEROLEOPHOBIC SURFACES AND APPLICATIONS THEREOF

(71) Applicant: GYRUS ACMI, INC., Westborough, MA (US)

(72) Inventors: Kester Julian Batchelor, Mound, MN (US); Teo Heng Jimmy Yang, Heath (GB)

(73) Assignee: Gyrus ACMI, Inc., Westborough, MA (US)

( * ) Notice: Subject to any disclaimer, the term of this patent is extended or adjusted under 35 U.S.C. 154(b) by 331 days.

(21) Appl. No.: 18/262,495

(22) PCT Filed: Jan. 20, 2022

(86) PCT No.: PCT/US2022/070275
§ 371 (c)(1),
(2) Date: Jul. 21, 2023

(87) PCT Pub. No.: WO2022/159965
PCT Pub. Date: Jul. 28, 2022

(65) Prior Publication Data
US 2024/0315754 A1 Sep. 26, 2024

Related U.S. Application Data

(60) Provisional application No. 63/139,845, filed on Jan. 21, 2021.

(51) Int. Cl.
*A61B 18/12* (2006.01)
*A61B 18/00* (2006.01)
(Continued)

(52) U.S. Cl.
CPC ............. *A61B 18/12* (2013.01); *A61B 90/08* (2016.02); *B08B 17/065* (2013.01);
(Continued)

(58) Field of Classification Search
CPC .................... A61B 18/12; A61B 90/08; A61B 2018/00077; A61B 2018/00083;
(Continued)

(56) References Cited

U.S. PATENT DOCUMENTS 5,169,397 A 12/1992 Sakashita et al.
6,923,757 B2 8/2005 Abe et al.
(Continued)

FOREIGN PATENT DOCUMENTS

CN 117320649 A 12/2023
JP H0564661 A 3/1993
(Continued)

OTHER PUBLICATIONS

"International Application Serial No. PCT/US2022/070275, International Search Report mailed May 4, 2022", 4 pgs.
(Continued)

*Primary Examiner* — Donald M Flores, Jr.
(74) *Attorney, Agent, or Firm* — Schwegman Lundberg & Woessner, P.A

(57) ABSTRACT
Various aspects disclosed relate to an article such as a medical device, a treatment device, or a surgical device. The article includes a substrate and a superhydrophobic or superhydrophobic portion disposed on a surface of the substrate. The superhydrophobic or superoleophobic portion, the substrate, or both are substantially transparent, comprise a color, or both.

16 Claims, 3 Drawing Sheets

(51) Int. Cl.
  *A61B 90/00* (2016.01)
  *B08B 17/06* (2006.01)
(52) U.S. Cl.
  CPC .............. *A61B 2018/00077* (2013.01); *A61B 2018/00083* (2013.01); *A61B 2018/0063* (2013.01); *A61B 2090/0807* (2016.02); *Y10T 428/24355* (2015.01); *Y10T 428/24364* (2015.01)
(58) Field of Classification Search
  CPC .... A61B 2018/0063; A61B 2090/0807; A61B 2017/00938; B08B 17/065; Y10T 428/24355; Y10T 428/24364
  See application file for complete search history.

(56) References Cited

U.S. PATENT DOCUMENTS

| | | | | |
|---|---|---|---|---|
| 2002/0128539 | A1* | 9/2002 | Higuma | G02B 23/2453 600/162 |
| 2005/0273126 | A1* | 12/2005 | Beaupre | A61B 17/320068 606/169 |
| 2006/0058583 | A1 | 3/2006 | Matsumoto et al. | |
| 2007/0005024 | A1 | 1/2007 | Weber et al. | |
| 2008/0221390 | A1 | 9/2008 | Bob | |
| 2009/0030280 | A1* | 1/2009 | Matsumoto | A61B 1/005 600/121 |
| 2011/0177252 | A1* | 7/2011 | Kanagasabapathy | C09D 5/1618 977/773 |
| 2015/0044421 | A1* | 2/2015 | Hassan | C04B 41/91 428/141 |
| 2015/0336360 | A1 | 11/2015 | Bhushan et al. | |
| 2021/0321861 | A1 | 10/2021 | Mcweeney et al. | |

FOREIGN PATENT DOCUMENTS

| | | |
|---|---|---|
| JP | 2706507 B2 | 10/1997 |
| JP | 2971490 B2 | 11/1999 |
| JP | 3469770 B2 | 11/2003 |
| KR | 20120127917 A | 11/2012 |
| WO | WO-2022159965 A1 | 7/2022 |
| WO | WO-2022159965 A9 | 6/2023 |

OTHER PUBLICATIONS

"International Application Serial No. PCT/US2022/070275, Written Opinion mailed May 4, 2022", 8 pgs.

"Chinese Application Serial No. 202280015376.2, Notification to Make Rectification (210302) mailed Sep. 21, 2023", w/o English Translation, 1 page.

"Chinese Application Serial No. 202280015376.2, Response filed Nov. 20, 2023 to Notification to Make Rectification (210302) mailed Sep. 21, 2023", W/O English Claims, 1 page.

"International Application Serial No. PCT/US2022/070275, International Preliminary Report on Patentability mailed Aug. 3, 2023", 10 pgs.

* cited by examiner

SUPERHYDROPHOBIC OR SUPEROLEOPHOBIC SURFACES AND APPLICATIONS THEREOF

CROSS REFERENCE TO RELATED APPLICATION

This application is a U.S. national stage filing under 35 U.S.C. § 371 from International Application No. PCT/US2022/070275, titled "SUPERHYDROPHOBIC OR SUPEROLEOPHOBIC SURFACES AND APPLICATIONS THEREOF." filed on Jan. 20, 2022, and published as WO 2022/159965 on Jul. 28, 2022, which claims priority to United States Provisional Patent Application No. 63/139, 845, titled "SUPERHYDROPHOBIC OR SUPEROLEOPHOBIC SURFACES AND APPLICATIONS THEREOF," filed on Jan. 21, 2021, the benefit of priority of each of which is claimed herein, and which applications and publication are hereby incorporated by reference in their entirety.

TECHNICAL FIELD

This disclosure generally relates to medical devices used in surgical applications.

SUMMARY OF THE INVENTION

Surfaces on medical devices or other industrial articles can be exposed to a wide variety of liquids. Accumulation of these liquids can cause significant damage or impair the operability of the device or article. It is, therefore, desirable to modify these devices or articles to mitigate the accumulation of liquids.

The present disclosure includes a superhydrophobic or superoleophobic article. The article includes a substrate and a superhydrophobic or superoleophobic portion disposed on a surface of the substrate. The superhydrophobic or superoleophobic portion, the substrate, or both are substantially transparent, comprise a color, or both.

The present disclosure further includes a superhydrophobic or superoleophobic article. The article includes a substrate and a superhydrophobic or superoleophobic portion disposed on a surface of the substrate. The superhydrophobic or superoleophobic portion is at least partially disposed on a surface of the substrate and includes tungsten disulfide, hexamethyldisiloxane, tetramethyldisiloxane, fluorosilane, a glass, a perfluoropolyether, manganese oxide polystyrene, zinc oxide polystyrene, precipitated calcium carbonate, or a mixture thereof. The superhydrophobic or superoleophobic portion further includes a structural microstructure, a structural nanostructure, or a combination thereof.

The present disclosure further includes a method of making a superhydrophobic or superoleophobic article. The article includes a substrate and a superhydrophobic or superoleophobic portion disposed on a surface of the substrate. The superhydrophobic or superoleophobic portion, the substrate, or both are substantially transparent, comprise a color, or both. The method includes disposing the superhydrophobic or superoleophobic portion on at least a portion of the substrate.

BRIEF DESCRIPTION OF THE FIGURES

The drawings illustrate generally, by way of example, but not by way of limitation, various embodiments of the present invention.

DETAILED DESCRIPTION OF THE INVENTION

Figure 1:
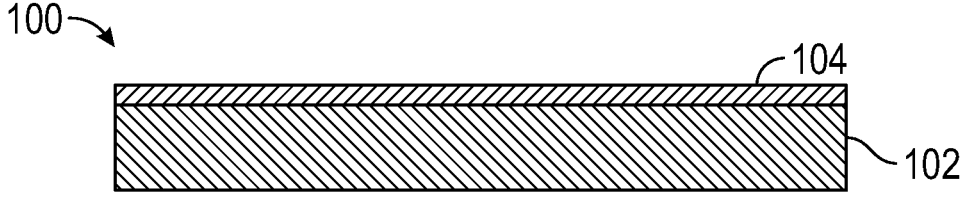
FIG. 1 is a sectional view of an article that includes a substrate and a superhydrophobic or superoleophobic portion.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range. The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that about 0 wt % to about 5 wt % of the composition is the material, or about 0 wt % to about 1 wt %, or about 5 wt % or less, or less than or equal to about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

The polymers described herein can terminate in any suitable way. In some embodiments, the polymers can terminate with an end group that is independently chosen from a suitable polymerization initiator, —H, —OH, a substituted or unsubstituted $(C_1-C_{20})$hydrocarbyl (e.g., $(C_1-C_{10})$alkyl or $(C_6-C_{20})$aryl) interrupted with 0, 1, 2, or 3 groups independently selected from —O—, substituted or unsubstituted —NH—, and —S—, a poly(substituted or unsubstituted $(C_1-C_{20})$hydrocarbyloxy), and a poly(substituted or unsubstituted $(C_1-C_{20})$hydrocarbylamino).

The inventors have discovered that accumulation of a liquid on an article may obscure a surface (e.g., make it difficult to read a symbol a word or image), render certain features inoperable (e.g., interfere with a function of the article), damage the article (e.g., damage an electrical component of an article), or any combination thereof. Aspects described herein are beneficial for numerous types devices, especially for devices used in messy environments. In one non-limiting example, aspects find particular use in medical devices where actuators, such as buttons and the like used in messy environments such as surgery and other tissue treatments or visualizations. Blood can be particularly obscuring in such environments due to its opacity, viscosity and adherence to surfaces.

Disclosed herein are various aspects relating to articles or assemblies that are superhydrophobic, superoleophobic, or both. That is, as used herein, in the detailed description and claims, any article or portion that is superhydrophobic or superoleophobic, can also be both superhydrophobic and superoleophobic. Examples of suitable articles or assemblies can include a medical device, an electronic device, or an industrial surface. Examples of these are described further herein. In operation, the superhydrophobic or superoleophobic portion can help to quickly and effectively prevent accumulation of a water-based or oil-based liquid from collecting in a substantial amount at certain locations on the article or assembly.

As used herein, superhydrophobic (alternatively known as ultrahydrophobic) can refer to surfaces or portions of a surface that are highly hydrophobic (e.g., extremely difficult to wet). The contact angles of a water droplet on superhydrophobic material generally exceed 150. This can be referred to as the "lotus effect," so named after the superhydrophobic leaves of the lotus plant. A droplet striking these kinds of surfaces can fully rebound like an elastic ball. Interactions of bouncing drops can be further reduced using special superhydrophobic surfaces that promote symmetry breaking, pancake bouncing or waterbowl bouncing. As used herein superoleophobic is a phenomenon where the contact angles of various oil droplets with low surface tension on a solid surface are larger than 150°.

According to various aspects, a superhydrophobic or superoleophobic article includes at least a substrate and a superhydrophobic or superoleophobic portion. FIG. 1 is a sectional view of an article 100 that includes substrate 102 and superhydrophobic or superoleophobic portion or coating 104. The superhydrophobic or superoleophobic portion 104 is disposed over at least a portion of the substrate. For example, the superhydrophobic or superoleophobic portion 104 can be disposed over about 1% total surface area of the substrate 102 to about 100% total surface are of the substrate 102, about 5% total surface area of the substrate 102 to about 95% total surface area of the substrate 102, about 10% total surface area of the substrate 102 to about 90% total surface area of the substrate 102, about 15% total surface area of the substrate 102 to about 85% total surface area of the substrate 102, about 20% total surface area of the substrate 102 to about 80% total surface area of the substrate 102, about 25% total surface area of the substrate 102 to about 75% total surface area of the substrate 102, about 30% total surface area of the substrate 102 to about 70% total surface area of the substrate 102, about 35% total surface area of the substrate 102 to about 65% total surface area of the substrate 102, about 40% total surface area of the substrate 102 to about 60% total surface area of the substrate 102, about 45% total surface area of the substrate 102 to about 65% total surface area of the substrate 102, about 50% total surface area of the substrate 102 to about 60% total surface area of the substrate 102, or less than or equal to 100% total surface area of the substrate 102 and greater than or equal to 1, 5, 10, 15, 20, 25, 30, 35, 40, 45, 50, 55, 60, 65, 70, 75, 80, 85, 90, or 95% total surface area of the substrate 102. The superhydrophobic or superoleophobic portion 104 can take the form of being a coating formed from the same material or mixture of materials as the substrate 102 or at least the portion of the substrate 102 to which the superhydrophobic or superoleophobic portion 104 is applied. In other examples, the superhydrophobic or superoleophobic portion 104 can be integral to the substrate. In such an example, the superhydrophobic or superoleophobic portion 104 extends from the substrate 102.

The substrate 102 can include any suitable material or combination of materials. For example, the substrate 102 can include a metal, a plastic material, a ceramic, a glass, or a combination thereof. Suitable metals include iron, stainless steel, titanium, tantalum, platinum iridium, tungsten, copper, nickel, gold, aluminum, steel an alloy thereof, or a mixture thereof. Suitable plastic materials include a thermoplastic polymer a thermoset polymer, or a mixture thereof. Specific plastic materials can include a polyamide, a polycarbonate, a polyolefin, a polyester, a polyurethane, an epoxy, a copolymer thereof, or a mixture thereof. More specific plastics can include polytetrafluoroethylene, a styrene-butadiene copolymer, ethylene tetrafluoroethylene, a polyvinyl chloride, polyether urethane, a phenyl formaldehyde polymer, or a mixture thereof. Suitable examples of ceramics include yttria $(Y_2O_3)$, magnesia $(MgO)$, aluminum oxide $(Al_2O_3)$, a magnesium aluminum oxide $(MgAl_2O_4)$, a carbide, an oxy-carbide, a nitride, an oxynitride, a boride, an oxyboride, a sulfide, a selenide, a sulfo-selenide, silica, zirconia, silicon-carbide, silicon-nitride, aluminum nitride, or a mixture thereof. Suitable examples of glass include soda lime silicate glass, alkali aluminosilicate glass, alkali containing boro-silicate glass, alkali aluminophosphosilicate glass, alkali aluminoborosilicate glass, or a mixture thereof.

The substrate 102 can be a flexible or a rigid structure. The substrate 102 can be substantially planar or non-planar. Examples of suitable non-planar substrates can include a curved substrate or an undulating substrate. In some examples, the substrate 102 can have a planar portion along with a rounded portion, an undulating portion, or both.

The superhydrophobic or superoleophobic portion 104 can include a metal, a polymeric material, a ceramic, a glass, or a combination thereof. Suitable metals include iron, stainless steel, titanium, tantalum, platinum Iridium, tungsten, copper, nickel, gold, aluminum, steel an alloy thereof, or a mixture thereof. Suitable polymeric materials include a thermoplastic polymer a thermoset polymer, or a mixture thereof. Specific plastic materials can include a polyamide, a polycarbonate, a polyolefin, a polyester, a polyurethane, an epoxy, a copolymer thereof, or a mixture thereof. More specific plastics can include polytetrafluoroethylene, a styrene-butadiene copolymer, ethylene tetrafluoroethylene, a polyvinyl chloride, polyether urethane, a phenyl formaldehyde polymer, or a mixture thereof. Suitable examples of glass include soda lime silicate glass, alkali aluminosilicate glass, alkali containing borosilicate glass, alkali aluminophosphosilicate glass, alkali aluminoborosilicate glass, or a mixture thereof. Specific examples of materials for the superhydrophobic or superoleophobic portion 104 can include tungsten disulfide, hexamethyldisiloxane, tetramethyldisiloxane, fluorosilane, a glass, a perfluoropolyether, manganese oxide polystyrene, zinc oxide polystyrene, precipitated calcium carbonate, or a mixture thereof.

The superhydrophobic or superoleophobic properties of the superhydrophobic or superoleophobic portion 104 can be a result of the superhydrophobic or superoleophobic portion 104's structure. For example, the superhydrophobic or superoleophobic portion 104 can include a plurality of microstructures, a plurality of nanostructures, or a combination thereof. In various examples, the plurality of structural features are microstructures and independently have a major dimension in a range of from about 1 μm to about 1000 μm, about 250 μm to about 750 μm, about 400 μm to about 600 μm, less than, equal to, or greater than about 1 μm, 25, 50, 75, 100, 125, 150, 175, 200, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or about 1000 μm. In various examples, the plurality of structural features are nanostructures and independently have a major dimension in a range of from about 1 nm to about 100 nm, about 10 nm to about 70 nm, about 30 nm to about 50 nm, less than, equal to, or greater than about 1 nm, 5, 10, 15, 20, 25, 30, 35, 40, 45, 50, 55, 60, 65, 70, 75, 80, 85, 90, 95, or about 100 nm. In various aspects a variable thickness of the superhydrophobic or superoleophobic portion 104 can result from imperfections imparted during manufacturing.

Any microstructure or nanostructure can be a structural component of the article 100. The microstructure or nanostructure can conform to any suitable shape. For example, an individual microstructure can be shaped as a microwire, a microrod, a microtube, a microsphere, or a microdroplet. In some examples, an individual nanostructure can be shaped as a nanowire, a nanorod, a nanotube, a nanosphere, or a nanodroplet.

In examples that include a plurality of microstructures, a plurality of nanostructures, or a mixture thereof, a pitch between adjacent structural features can be constant across the article. Alternatively, a pitch between adjacent structural features is variable across the article. In some examples, a pitch between adjacent structural features of a first plurality of structural features is constant and a pitch between adjacent structural features of a second plurality of structural features is variable.

A thickness of the superhydrophobic or superoleophobic portion 104 can generally be in a range of from about 0.1 nm to about 15 nm, about 5 nm to about 10 nm, less than, equal to, or greater than about 0.1 nm, 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or about 15 nm. In some examples, a thickness of the superhydrophobic or superoleophobic portion 104 is substantially constant across the article. In some other examples, the thickness of the superhydrophobic or superoleophobic portion 104 is variable. In examples where the thickness the superhydrophobic or superoleophobic portion 104 is variable across the article, the thickness values described herein can be an average thickness value, a median thickness value, or representative of the major thickness value.

Figure 2:
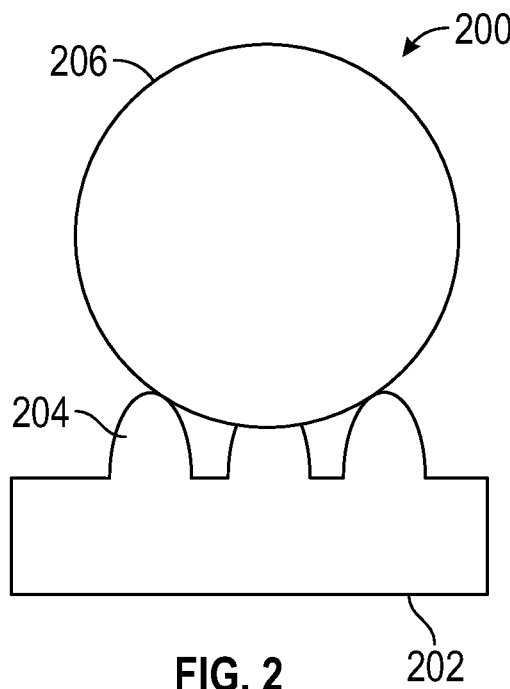
FIG. 2 is a sectional view of an article that includes a substrate and a superhydrophobic or superoleophobic portion including a plurality of microfeatures.

FIG. 2 is a schematic view of an article 200. The article 200 includes the substrate 202. The substrate 202 can include any material or materials describe herein with respect to the substrate 102. The article 200 further includes the superhydrophobic or superoleophobic portion 204. The superhydrophobic or superoleophobic portion 204 can include any material or materials described herein with respect to the superhydrophobic or superoleophobic portion 104. As shown, the superhydrophobic or superoleophobic portion 204 includes a plurality of microstructures. FIG. 2 further shows droplet 206. Droplet 206 can be a water droplet or an oil droplet.

Figure 3:
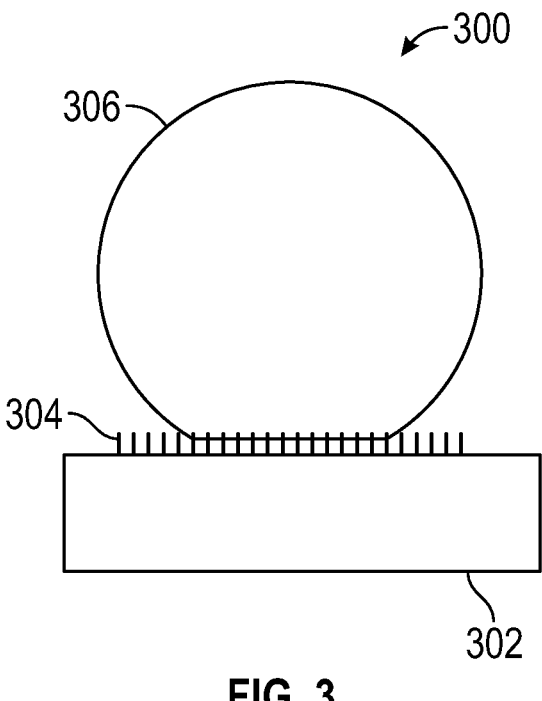
FIG. 3 is a sectional view of an article that includes a substrate and a superhydrophobic or superoleophobic portion including a plurality of nanofeatures.

FIG. 3 is a schematic view of an article 300. The article 300 includes the substrate 302. The substrate 302 can include any material or materials describe herein with respect to the substrate 102. The article 300 further includes the superhydrophobic or superoleophobic portion 304. The superhydrophobic or superoleophobic portion 304 can include any material or materials described herein with respect to the superhydrophobic or superoleophobic portion 104. As shown, the superhydrophobic or superoleophobic portion 304 includes a plurality of nanostructures. FIG. 3 further shows droplet 306. Droplet 206 can be a water droplet or an oil droplet.

Figure 4:
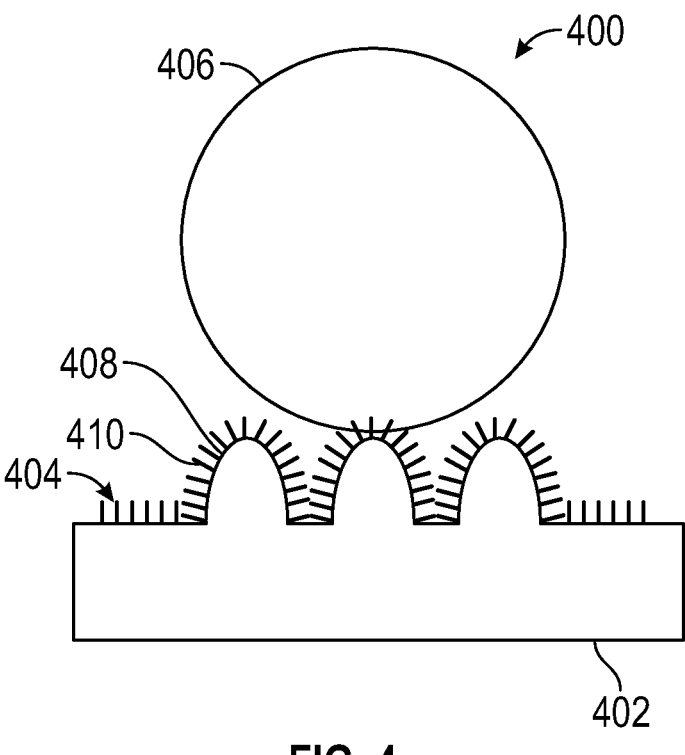
FIG. 4 is a sectional view of an article that includes a substrate and a superhydrophobic or superoleophobic portion including a plurality hierarchical features arranged as microfeatures and nanofeatures.

FIG. 4 is a schematic view of an article 400. The article 400 includes the substrate 402. The substrate 402 can include any material or materials describe herein with respect to the substrate 102. The article 400 further includes the superhydrophobic or superoleophobic portion 404. The superhydrophobic or superoleophobic portion 404 can include any material or materials described herein with respect to the superhydrophobic or superoleophobic portion 104. As shown, the superhydrophobic or superoleophobic portion 404 includes a plurality of microstructures 408 and nanostructures 410. As further shown, a portion of the nanostructures 410 are disposed on, or extend from, the microstructures 408. FIG. 3 further shows droplet 406. Droplet 406 can be a water droplet or an oil droplet. The structure shown for the superhydrophobic or superoleophobic portion 404 can be generally referred to as a hierarchical structure. It has been found that the hierarchical structures can proved particularly exceptional superhydrophobic or superoleophobic properties.

Although not shown, in some examples, an adhesive layer can be disposed between the superhydrophobic or superoleophobic portion 104 and the substrate 102 (superhydrophobic or superoleophobic portion 104 and substrate 102 are mentioned here for brevity but the teachings mentioned herein can apply equally to superhydrophobic or superoleophobic portions 204, 304 and 404 as well as substrates 202, 302, and 402). Including an adhesive layer can be helpful in examples, where the superhydrophobic or superoleophobic portion 104 and the substrate 102 include different materials or mixtures of materials. Examples of suitable adhesives in the adhesive layer can include a pressure-sensitive adhesive, an epoxy resin, or a mixture thereof. In some examples, adhesion can be enhanced by roughing or etching the portion of the substrate that contacts the superhydrophobic or superoleophobic portion 104, the portion of the superhydrophobic or superoleophobic portion 104 that contacts the substrate, or both. Roughing or etching can be accomplished using e-beam radiation, a chemical etchant (e.g., an acid), or a combination thereof.

The superhydrophobic or superoleophobic portion 104 described herein can be continuously distributed about the substrate. However, in some examples, the superhydrophobic or superoleophobic portion 104 can be discontinuously distributed about the substrate. For example, the superhydrophobic or superoleophobic portion 104 can be a first superhydrophobic or superoleophobic portion 104 and the article 100 can further include a second superhydrophobic or superoleophobic portion adjacent to the first superhydrophobic or superoleophobic portion. In still further examples, the superhydrophobic or superoleophobic portion 104 can include any plural number of superhydrophobic or superoleophobic portions 104.

In examples that include multiple superhydrophobic or superoleophobic portions 104, the respective superhydrophobic or superoleophobic portions 104 can include the same material or combination of materials. Conversely, the respective superhydrophobic or superoleophobic portions 104 can include a different material or combination of materials. Additionally, the respective superhydrophobic or superoleophobic portions 104 can include identical microstructures, nanostructures, or combinations of microstructures and nanostructures. However, in some examples, the respective superhydrophobic or superoleophobic portions 104 can include different microstructures, nanostructures, or combinations of microstructures and nanostructures.

The material of the superhydrophobic or superoleophobic, microstructure, nanostructure, combined microstructure and nanostructure, or any combination thereof of the superhydrophobic or superoleophobic structure can result in the article having a desired contact angle. The contact angle can be a measure of the average value of contact angles measured across the article or an absolute value thereof. Alternatively, the contact angle can be a measure of the average value of contact angles measured across the superhydrophobic or superoleophobic portion 104 or an absolute value thereof. According to various aspects, a contact angle can be at least 120 degrees, as determined using ASTM D7334-08, at least 130 degrees, at least 140 degrees, at least 150 degrees, at least 160 degrees, at least 170 degrees, at least 180 degrees in a range of from about 120 degrees to about 180 degrees, about 130 degrees to about 170 degrees, or about 140 degrees to about 160 degrees.

The articles 100 described herein can take on many different forms. For example, the article can be a medical device, an electronic device, or an industrial surface. Examples of suitable medical devices can include a cauterizer, a cutting forceps, a ventilator, a pacemaker, a stent, a catheter, a hearing aid, a prosthesis, a joint replacement, a mesh, a staple, a guide wire, an endoscope, or a combination thereof. Examples of electronic devices can include a microscope, a generator, a mobile telephone, a tablet computer, a laptop computer, a desktop computer, a light generator, a speaker, a lens, a screen, or a combination thereof. Examples of an industrial surface include a lab bench, an assembly line surface, a wall covering, a kitchen countertop, a doped paint, a mirror, a light fitting, a windshield, a window, an automobile surface, a pipe coating, or a combination thereof.

Including the superhydrophobic or superoleophobic portion 104 in any of the articles described herein can help to enhance the ability of the respective article to repel water, a water-based liquid, an oil, an oil-based liquid, or a mixture thereof from accumulating on the article or a portion thereof. Preventing this accumulation can be beneficial in that a user simply may not want liquids to accumulate on an article. For example, accumulation of a liquid on an article may obscure a surface (e.g., make it difficult to read a symbol a word or image), render certain features inoperable (e.g., interfere with a function of the article), damage the article (e.g., damage an electrical component of an article), or any combination thereof.

In some specific examples, the superhydrophobic or superoleophobic portion 104 can form, in whole or in part, or be disposed on a button, a trigger, a graphical user interface, a visual indicia (e.g., a word, a number, a pattern, a picture, a color, or a combination thereof), or a combination thereof. The superhydrophobic or superoleophobic portion 104 can be particularly useful, for example, in a medical device. A medical device can be routinely exposed to biological fluids. An example of a biological fluid to which a medical device can be exposed is blood. The biological fluid can adhere to the medical device, which can cause any number of problems. For example, the biological fluid may obscure a visual indicia or graphical user interface. Obscuring either of these could make it difficult for a user (e.g., physician) to read and understand the visual indicia. This can be problematic, for example, if the visual indicia indicates that a certain button engages, for example, a cutting feature, a cauterizing feature, or any other feature. Obscuring a graphical user interface can be problematic if a medical device uses the graphical user interface to deliver instructions to the user. Additionally, obscuring a graphical user interface can be problematic if the graphical user interface displays touch buttons to activate certain functions. Additionally, obscuring a trigger of a medical device can have many of the same drawbacks as mentioned herein with respect to buttons, with the addition that allowing a biological fluid to accumulate on a button or trigger can result in a slippery surface. A slippery surface on the button or trigger can make it difficult to press or pull the button or trigger as well as increase the risk of inadvertently pressing or pulling the button or trigger. In some examples, a medical device may include a haptic feature that allows a user to navigate the device by feeling the haptic features. Obscuring the haptic feature with a biological fluid, may make it difficult to feel the haptic feature correctly.

Including the superhydrophobic or superoleophobic portion 104 can help to address these drawbacks by providing a surface that mitigates the accumulation of the biological fluid thereon. In some examples, the superhydrophobic or superoleophobic portion 104 can be substantially transparent. If the superhydrophobic or superoleophobic portion 104 is substantially transparent, the superhydrophobic or superoleophobic portion 104 can be advantageously disposed over a visual indicia or graphical user interface so that the features thereof are substantially unobscured by the superhydrophobic or superoleophobic portion 104. In some examples, the superhydrophobic or superoleophobic portion 104 can include metal particles to allow the superhydrophobic or superoleophobic portion 104 to be electrically conductive, which can be helpful if the superhydrophobic or superoleophobic portion 104 is disposed over a graphical user interface that is a touch screen. Suitable metal particles include gold, silver, copper, alloys thereof, or combinations thereof.

In some examples, the substrate can include a pigment or a fluorophore. The pigment or fluorophore may be visible even if located underneath the superhydrophobic or superoleophobic portion 104 in examples in which the superhydrophobic or superoleophobic portion 104 is substantially transparent or even translucent. In some examples, the superhydrophobic or superoleophobic portion 104 can include a pigment, a fluorophore, or both. The color provided by the pigment, fluorophore or both can help to indicate a function of a portion of the medical device. Including the superhydrophobic or superoleophobic portion 104 helps to keep the color resulting from the pigment, fluorophore, or both from being obstructed by the biological fluid.

In some examples, a protective layer can be disposed over the superhydrophobic or superoleophobic portion 104. The protective layer can help to protect the superhydrophobic or superoleophobic portion 104 for a desired amount of time (e.g., during shipping or storage of an article that includes the superhydrophobic or superoleophobic portion 104). The protective layer can be removed prior to using the article. Removal can include peeling or degrading the protective layer. Degrading the protective layer can include exposing the protective layer to a reactant capable of dissolving the protective layer or to an etchant. In some examples the protective layer can be designed to degrade over a set amount of time or upon exposure to a specific source of electromagnetic radiation (e.g., having a certain wavelength). In some examples, the protective layer can include a clear coat disposed over at least a portion of the superhydrophobic or superoleophobic portion 104.

Figures 5A, 5B:
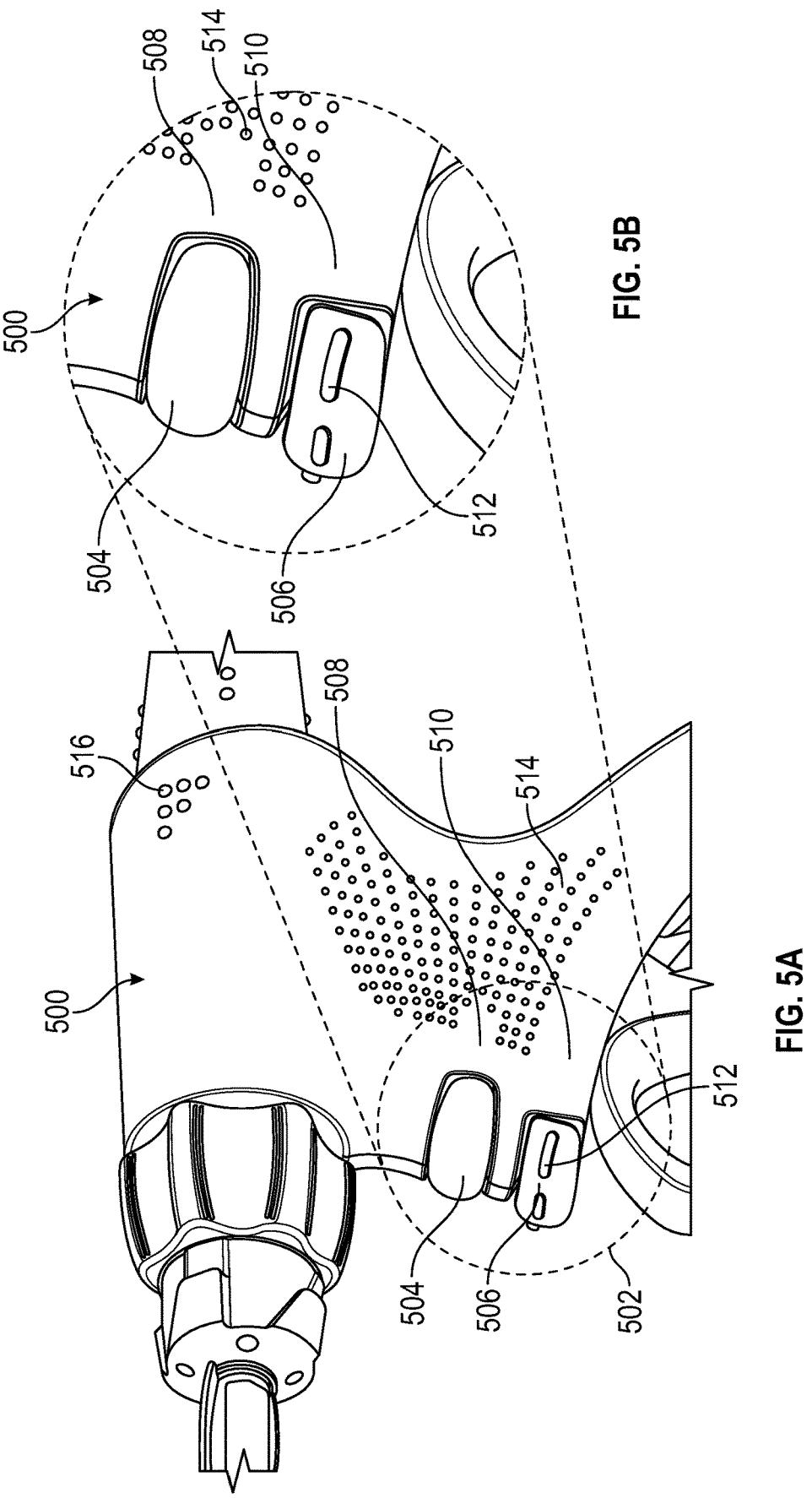
FIG. 5A is perspective view of an electrosurgical device including the superhydrophobic or superoleophobic portion.
FIG. 5B is a zoomed view of a portion of the electrosurgical device of FIG. 5B.

FIG. 5A shows a device 500. The device 500 is an electrosurgical device, more specifically an electrosurgical vessel sealing device. Although an electrosurgical vessel sealing device is described, the teachings of the instant disclosure are applicable to a broad range of other medical devices. FIG. 5B isolates and enlarges a section 502 of the device 500. As shown, the device 500 includes a first button 504 and a second button 506. The device further includes a first visual image (the phrase "SEAL & CUT") 508 and a second visual image (the word "SEAL") 510. The device 500 further includes a first group of haptic features 512, a second group of haptic features 514, and a third group of haptic features 516.

The superhydrophobic or superoleophobic coating 104 (e.g., superhydrophobic or superoleophobic coating 204, 304, 404, or a combination thereof) can be applied to the first button, 504, the second button 506, the first visual image 508, the second visual image 510, the first group of haptic features 512, the second group of haptic features 514, the third group of haptic features 516, portions thereof, and combinations thereof. If the superhydrophobic or superoleophobic coating 104 is applied to any of the components described herein, the superhydrophobic or superoleophobic coating 104 can be substantially transparent or translucent so as not to obscure the visual image (e.g., the first visual image 508 or the second visual image 510), or block a color (e.g., the pink color of the first button 504 or the blue color of the second button 506). Alternatively, the superhydrophobic or superoleophobic coating 104 can include a pigment or colorant that provides, in whole or in part, the pink color of the first button 504 or the blue color of the second button 506.

The article can be manufactured according to many suitable methods. As an example of a suitable method, the superhydrophobic or superoleophobic portion 104 can be disposed over at least a portion of the substrate. Examples of suitable disposing techniques include a sol-gel coating process, a cold spray coating process, chemical vapor deposition, physical vapor deposition, a thermal spray deposition, an in situ polymerization (e.g., plasma polymerization), a spin-coating deposition, a dip-coating deposition, an electrodeposition, additive manufacturing, or a combination thereof. The nanofeatures, microfeatures, or both as described above, can be formed during the disposing step. Alternatively, the nanofeatures, microfeatures, or both can be formed in an additional step such as molding, imprinting, etching, or a combination thereof, to impart the structural microstructure feature, structural nanostructure feature, or a combination thereof.

As described herein above, the superhydrophobic or superoleophobic portion 104 can be disposed over the entire surface area of the substrate or over a portion of the substrate. The superhydrophobic or superoleophobic portion 104 can be disposed over the surface of the substrate in a random or predetermined pattern. In some examples, a mask can be disposed over the substrate to help ensure that the superhydrophobic or superoleophobic portion 104 is only disposed over discrete locations on the substrate. In other examples, disposing the superhydrophobic or superoleophobic portion 104 can be disposed by hand or by a machine at a selected location or selected locations on the substrate.

As mentioned herein, in some examples, the superhydrophobic or superoleophobic portion 104 can be integral to the substrate. In these examples the superhydrophobic or superoleophobic portion 104 can be formed by molding the substrate, imprinting the substrate, etching the substrate, or a combination thereof, to impart the structural microstructure feature, structural nanostructure feature, or a combination thereof to the substrate. In some examples, processability of the substrate can be enhanced by softening the substrate. For example, if the substrate includes a polymeric material, the substrate can be heated to make the substrate more malleable and deformable so that the microstructures, nanostructures, or both can be imprinted thereon.

Exemplary Aspects

The following exemplary aspects are provided, the numbering of which is not to be construed as designating levels of importance:

Aspect 1 provides an article comprising:

a substrate; and a superhydrophobic or superoleophobic portion disposed on a surface of the substrate, wherein the superhydrophobic or superoleophobic portion comprises a button, a trigger, a graphical user interface, the visual indicia, or a combination thereof and further comprises a pigment providing a visual indicia, and the article comprises a medical device, a treatment device, or a surgical device.

Aspect 2 provides an article comprising:

a substrate comprising a visual indicia; and a superhydrophobic or superoleophobic portion disposed on a surface of the substrate, wherein the superhydrophobic or superoleophobic portion a button, a trigger, a graphical user interface, the visual indicia, or a combination thereof is substantially transparent or substantially translucent allowing the visual indicia of the substrate to be visible therethrough, and the article comprises a medical device, a treatment device, or a surgical device.

Aspect 3 provides the article of any one of Aspects 1 or 2, wherein the substrate comprises a metal, a plastic material, a ceramic, a glass, or a combination thereof.

Aspect 4 provides the article of Aspect 3, wherein the metal comprises iron, stainless steel, titanium, tantalum, platinum, iridium, tungsten, copper, nickel, gold, aluminum, steel an alloy thereof, or a mixture thereof.

Aspect 5 provides the article of any one of Aspects 3 or 4, wherein the plastic material comprises a thermoplastic polymer a thermoset polymer, or a mixture thereof.

Aspect 6 provides the article of any one of Aspects 3-5, wherein the plastic material comprises a polyamide, a polycarbonate, a polyolefin, a polyester, a polyurethane, an epoxy, a copolymer thereof, or a mixture thereof.

Aspect 7 provides the article of any one of Aspects 3-6, wherein the plastic material comprises polytetrafluoroethylene, a styrene-butadiene copolymer, ethylene tetrafluoroethylene, a polyvinyl chloride, polyether urethane, a phenyl formaldehyde polymer, or a mixture thereof.

Aspect 8 provides the article of any one of Aspects 3-7, wherein the ceramic comprises yttria ($Y_2O_3$), magnesia (MgO), aluminum oxide ($Al_2O_3$), a magnesium aluminum oxide ($MgAl_2O_4$), a carbide, an oxycarbide, a nitride, an oxynitride, a boride, an oxyboride, a sulfide, a selenide, a sulfo-selenide, silica, zirconia, silicon-carbide, silicon-nitride, aluminum nitride, or a mixture thereof.

Aspect 9 provides the article of any one of Aspects 3-8, wherein the glass comprises soda lime silicate glass, alkali aluminosilicate glass, alkali containing borosilicate glass, alkali aluminophosphosilicate glass, alkali aluminoborosilicate glass, or a mixture thereof.

Aspect 10 provides the article of any one of Aspects 1-9, wherein the superhydrophobic or superoleophobic portion comprises a superhydrophobic or superoleophobic material comprising a metal, a polymeric material, a ceramic, a glass, or a combination thereof.

Aspect 11 provides the article of Aspect 10, wherein the superhydrophobic or superoleophobic portion comprises tungsten disulfide, hexamethyldisiloxane, tetramethyldisiloxane, fluorosilane, a glass, a perfluoropolyether, manganese oxide polystyrene, zinc oxide polystyrene, precipitated calcium carbonate, or a mixture thereof.

Aspect 12 provides the article of any one of Aspects 1-11, wherein the superhydrophobic or superoleophobic portion comprises a microstructure, a nanostructure, or a combination thereof.

Aspect 13 provides the article of Aspect 12, wherein the microstructure comprises a plurality of structural features independently having a major dimension in a range of from about 1 μm to about 1000 μm.

Aspect 14 provides the article of any one of Aspects 12 or 13, wherein the microstructure comprises a plurality of structural features independently having a major dimension in a range of from about 250 μm to about 750 μm.

Aspect 15 provides the article of any one of Aspects 12-14, wherein the nanostructure comprises a plurality of structural features independently having a major dimension in a range of from about 1 nm to about 100 nm.

Aspect 16 provides the article of any one of Aspects 12-15, wherein the nanostructure comprises a plurality of structural features independently having a major dimension in a range of from about 10 nm to about 70 nm.

Aspect 17 provides the article of any one of Aspects 12-16, wherein the superhydrophobic or superoleophobic portion comprises a plurality of structural microfeatures and a plurality of structural nanofeatures.

Aspect 18 provides the article of Aspect 17, wherein the plurality of nanostructures extend from the plurality of microstructures and are a substrate to the plurality of nanostructures.

Aspect 19 provides the article of any one of Aspects 12-18, wherein the microstructure comprises a microwire, a microrod, a microtube, a microsphere, or a microdroplet.

Aspect 20 provides the article of any one of Aspects 12-19, wherein the nanostructure comprises a nanowire, a nanorod, a nanotube, a nanosphere, or a nanodroplet.

Aspect 21 provides the article of any one of Aspects 13-20, wherein a pitch between adjacent structural features is constant across the article.

Aspect 22 provides the article of any one of Aspects 13-21, wherein a pitch between adjacent structural features is variable across the article.

Aspect 23 provides the article of any one of Aspects 13-22, wherein a pitch between adjacent structural features of a first plurality of structural features is constant and a pitch between adjacent structural features of a second plurality of structural features is variable.

Aspect 24 provides the article of any one of Aspects 12-23, wherein the microstructure, nanostructure, or a mixture thereof comprise the superhydrophobic or superoleophobic material.

Aspect 25 provides the article of any one of Aspects 1-24, where a thickness of the superhydrophobic or superoleophobic portion is in a range of from about 0.1 nm to about 15 nm.

Aspect 26 provides the article of Aspect 25, where a thickness of the superhydrophobic or superoleophobic portion is in a range of from about 5 nm to about 10 nm.

Aspect 27 provides the article of any one of Aspects 25 or 26, wherein the thickness of the superhydrophobic or superoleophobic portion is substantially constant across the article.

Aspect 28 provides the article of any one of Aspects 25 or 26, wherein the thickness of the superhydrophobic or superoleophobic portion is variable across the article.

Aspect 29 provides the article of any one of Aspects 1-28, further comprising an adhesive layer between the substrate and the superhydrophobic or superoleophobic portion.

Aspect 30 provides the article of Aspect 29, wherein the adhesive layer comprises a pressure sensitive adhesive.

Aspect 31 provides the article of any one of Aspects 1-30, wherein the superhydrophobic or superoleophobic portion is a first superhydrophobic or superoleophobic portion and the superhydrophobic or superoleophobic article further comprises a second superhydrophobic or superoleophobic portion adjacent to the first superhydrophobic or superoleophobic portion.

Aspect 32 provides the article of any one of Aspects 1-31, wherein a contact angle of the superhydrophobic or superoleophobic article is at least 120 degrees, as determined using ASTM D7334-08.

Aspect 33 provides the article of any one of Aspects 1-33, wherein a contact angle of the superhydrophobic or superoleophobic article is at least 150 degrees, as determined using ASTM D7334-08, as determined using ASTM D7334-08.

Aspect 34 provides the article of any one of Aspects 1-33, wherein a contact angle of the superhydrophobic or superoleophobic portion is in a range of from about 120 degrees to about 180 degrees, as determined using ASTM D7334-08.

Aspect 35 provides the article of any one of Aspects 1-34, wherein a contact angle of the superhydrophobic or superoleophobic portion is in a range of from about 140 degrees to about 160 degrees, as determined using ASTM D7334-08.

Aspect 36 provides the article of any one of Aspects 1-35, wherein the substrate is flexible.

Aspect 37 provides the article of any one of Aspects 1-36, wherein the superhydrophobic or superoleophobic portion, the substrate, or both are transparent.

Aspect 38 provides the article of any one of Aspects 1-37, wherein the superhydrophobic or superoleophobic portion, the substrate, or both comprise a pigment, a fluorophore, or both.

Aspect 39 provides the article of any one of Aspects 1-38, further comprising a clear coat disposed over at least a portion of the superhydrophobic or superoleophobic portion.

Aspect 40 provides the article of any one of Aspects 1-39, wherein the superhydrophobic or superoleophobic article is a medical device, an electronic device, or an industrial surface.

Aspect 41 provides the article of any one of Aspects 1-40, wherein the superhydrophobic or superoleophobic portion comprises a button, a trigger, or a combination thereof.

Aspect 42 provides the article of Aspect 41, wherein the visual indicia comprises a word, a number, a pattern, a picture, a color or a combination thereof.

Aspect 43 provides the article of any one of Aspects 1-42, wherein the superhydrophobic or superoleophobic portion further comprises a haptic feature.

Aspect 44 provides the article of any one of Aspects 1-43, wherein the medical device, the treatment device, or the surgical device comprises a cauterizer, a cutting forceps, a ventilator, a pacemaker, a stent, a catheter, a hearing aid, a prosthesis, a joint replacement, a mesh, a staple, a guide wire, an endoscope, a scalpel, or a combination thereof.

Aspect 45 provides an article comprising:

a substrate; and a superhydrophobic or superoleophobic portion at least partially disposed on a surface of the substrate, the superhydrophobic or superoleophobic portion comprising:

tungsten disulfide, hexamethyldisiloxane, tetramethyldisiloxane, fluorosilane, a glass, a perfluoropolyether, manganese oxide polystyrene, zinc oxide polystyrene, precipitated calcium carbonate, or a mixture thereof, and a structural microstructure, a structural nanostructure, or a combination thereof.

Aspect 46 provides the article of Aspect 45, wherein the substrate comprises a visual indicia and the superhydrophobic or superoleophobic portion is substantially transparent or substantially translucent.

Aspect 47 provides the article of Aspect 46, wherein the superhydrophobic or superoleophobic portion comprises a pigment providing a visual indicia.

Aspect 48 provides the article of any one of Aspects 45-47, wherein the article comprises a medical device, a treatment device, or a surgical device.

Aspect 49 provides the article of Aspect 48, wherein the medical device, the treatment device, or the surgical device comprises a cauterizer, a cutting forceps, a ventilator, a pacemaker, a stent, a catheter, a hearing aid, a prosthesis, a joint replacement, a mesh, a staple, a guide wire, an endoscope, a scalpel, or a combination thereof.

Aspect 50 provides a method of making the article, of any one of Aspects 1-49, the method comprising disposing the superhydrophobic or superoleophobic portion on at least a portion of the substrate.

Aspect 51 provides the method of Aspect 50, wherein disposing the disposing comprises a sol-gel coating process, a cold spray coating process, a chemical vapor deposition, a physical vapor deposition, a thermal spray deposition, an in situ polymerization, a spin-coating deposition, a dip-coating deposition, an electrodeposition, additive manufacturing, or a combination thereof.

Aspect 52 provides the method of any one of Aspects 50 or 51, further comprising molding, imprinting, etching, or a combination thereof, to impart the structural microstructure feature, structural nanostructure feature, or a combination thereof.

What is claimed is:

1. An article comprising:

a substrate; and a superhydrophobic or superoleophobic portion disposed on a surface of the substrate, wherein the superhydrophobic or superoleophobic portion comprises a button, a trigger, a graphical user interface, a visual indicia, or a combination thereof, wherein the visual indicia comprises a pigment, and the article comprises a medical device, a treatment device, or a surgical device and further comprises an adhesive layer between the substrate and the superhydrophobic or superoleophobic portion.

2. The article of claim 1, wherein the substrate comprises a metal, a plastic material, a ceramic, a glass, or a combination thereof.

3. The article of claim 2, wherein the plastic material comprises a thermoplastic polymer, a thermoset polymer, or a mixture thereof.

4. The article of claim 1, wherein the superhydrophobic or superoleophobic portion comprises a superhydrophobic or superoleophobic material comprising a metal, a polymeric material, a ceramic, a glass, or a combination thereof.

5. The article of claim 1, wherein the superhydrophobic or superoleophobic portion comprises tungsten disulfide, hexamethyldisiloxane, tetramethyldisiloxane, fluorosilane, a glass, a perfluoropolyether, manganese oxide polystyrene, zinc oxide polystyrene, precipitated calcium carbonate, or a mixture thereof.

6. The article of claim 1, wherein the superhydrophobic or superoleophobic portion comprises a microstructure, a nanostructure, or a combination thereof.

7. The article of claim 6, wherein the microstructure comprises a microwire, a microrod, a microtube, a microsphere, or a microdroplet.

8. The article of claim 6, wherein the nanostructure comprises a nanowire, a nanorod, a nanotube, a nanosphere, or a nanodroplet.

9. The article of claim 1, wherein the superhydrophobic or superoleophobic portion comprises a plurality of structural microfeatures and a plurality of structural nanofeatures.

10. The article of claim 1, wherein a contact angle of the superhydrophobic or superoleophobic portion is at least 120 degrees, as determined using ASTM D7334-08.

11. The article of claim 1, wherein the substrate is flexible.

12. The article of claim 1, wherein the superhydrophobic or superoleophobic portion, the substrate, or both are transparent.

13. The article of claim 1, wherein the superhydrophobic or superoleophobic portion, the substrate, or both comprise a second pigment, a fluorophore, or both.

14. The article of claim 1, wherein the superhydrophobic or superoleophobic portion comprises a button, a trigger, or a combination thereof.

15. An article comprising:

a substrate comprising a first visual indicia; and a superhydrophobic or superoleophobic portion disposed on a surface of the substrate, wherein the superhydrophobic or superoleophobic portion comprises a button, a trigger, a graphical user interface, a second visual indicia, or a combination thereof, and the superhydrophobic or superoleophobic portion is substantially transparent or substantially translucent allowing the first visual indicia of the substrate to be visible therethrough, and the article comprises a medical device, a treatment device, or a surgical device, wherein the superhydrophobic or superoleophobic portion comprises a microstructure, a nanostructure, or a combination thereof and the microstructure comprises a plurality of structural features independently having a major dimension in a range of from about 250 µm to about 750 µm.

16. The article of claim 15, wherein the plurality of nanostructures extend from the plurality of microstructures, and the plurality of microstructures are disposed on the surface of the substrate.

\* \* \* \* \*